(12) United States Patent
Oh et al.

(10) Patent No.: US 7,901,745 B2
(45) Date of Patent: Mar. 8, 2011

(54) 3,4-DICARBOXY-1,2,3,4-TETRAHYDRO-6-T-BUTYL-1-NAPHTHALENE-SUCCINIC DIANHYDRIDE AND LIQUID CRYSTAL ALIGNING AGENT COMPRISING POLYIMIDE RESIN PREPARED FROM THE DIANHYDRIDE

(75) Inventors: Jae Min Oh, Suwon (KR); Tae Hyoung Kwak, Goyang (KR); Ji Young Jeong, Seoul (KR)

(73) Assignee: Cheil Industries Inc., Gumi-si (KR)

( * ) Notice: Subject to any disclaimer, the term of this patent is extended or adjusted under 35 U.S.C. 154(b) by 87 days.

(21) Appl. No.: 12/476,465

(22) Filed: Jun. 2, 2009

(65) Prior Publication Data

US 2009/0299014 A1    Dec. 3, 2009

Related U.S. Application Data

(63) Continuation-in-part of application No. PCT/KR2007/006898, filed on Dec. 27, 2007.

(30) Foreign Application Priority Data

Apr. 11, 2007    (KR) .................. 10-2007-0035763

(51) Int. Cl.
*C09K 19/00*    (2006.01)
(52) U.S. Cl. ........ 428/1.26; 428/1.2; 525/420; 525/436; 528/332; 528/335; 528/350; 528/353; 528/363; 549/477; 562/488; 562/511; 562/887
(58) Field of Classification Search .............. 525/420, 525/436; 528/332, 335, 350, 353, 363; 549/477; 562/488, 511, 887; 428/1.2, 1.26
See application file for complete search history.

(56) References Cited

U.S. PATENT DOCUMENTS

| 3,574,160 | A | * | 4/1971 | Hsu et al. .................. 524/99 |
| 4,985,529 | A | * | 1/1991 | Saito et al. .................. 528/96 |
| 6,887,534 | B2 | | 5/2005 | Nakata et al. | |
| 2004/0009310 | A1 | * | 1/2004 | Nakata et al. .................. 428/1.2 |

FOREIGN PATENT DOCUMENTS

| JP | 2743460 A | 11/1990 |
| JP | 3322089 A | 3/1997 |
| JP | 10183120 A | 7/1998 |
| JP | 19047762 A | 2/2007 |
| KR | 2006-0115682 A | 11/2006 |
| WO | 2008/126978 A1 | 10/2008 |

OTHER PUBLICATIONS

International Search Report in counterpart International Application No. PCT/KR2007/006898, mailed Feb. 18, 2008.

* cited by examiner

*Primary Examiner* — David Wu
*Assistant Examiner* — Robert Jones
(74) *Attorney, Agent, or Firm* — Summa, Additon & Ashe, P.A.

(57) ABSTRACT

3,4-Dicarboxy-1,2,3,4-tetrahydro-6-t-butyl-1-naphthalene-succinic dianhydride is provided. The tetracarboxylic dianhydride is represented by Formula 1, which is described in the specification. Further provided is a liquid crystal aligning agent comprising a polyimide prepared using the tetracarboxylic dianhydride and a solvent. Further provided is a liquid crystal alignment layer formed using the liquid crystal aligning agent. The liquid crystal alignment layer exhibits excellent electro-optical properties and good processability in terms of printability.

18 Claims, 1 Drawing Sheet

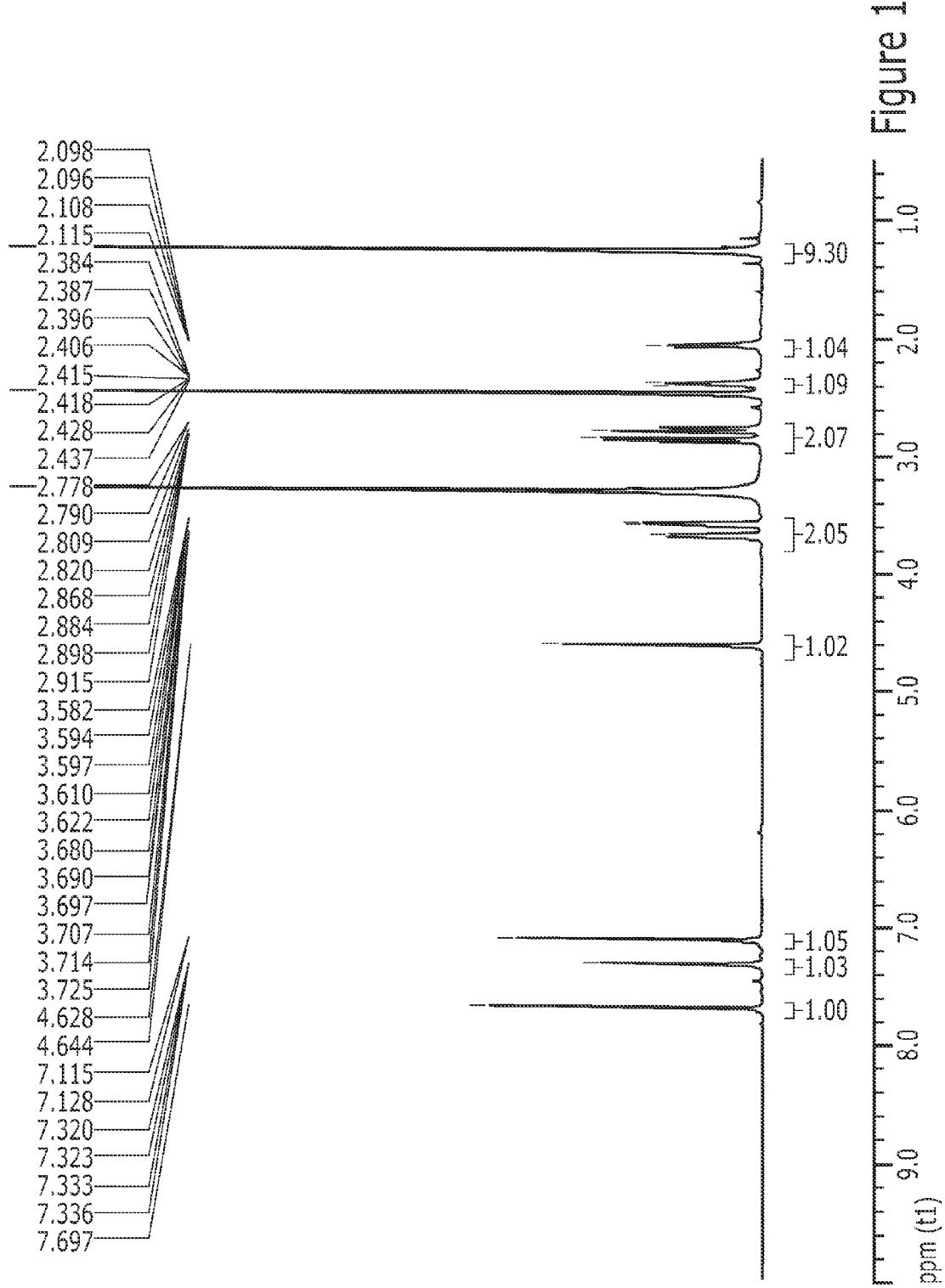

3,4-DICARBOXY-1,2,3,4-TETRAHYDRO-6-T-BUTYL-1-NAPHTHALENE-SUCCINIC DIANHYDRIDE AND LIQUID CRYSTAL ALIGNING AGENT COMPRISING POLYIMIDE RESIN PREPARED FROM THE DIANHYDRIDE

CROSS-REFERENCE TO RELATED APPLICATIONS

This non-provisional application is a continuation-in-part application of PCT Application No. PCT/KR2007/006898, filed Dec. 27, 2007, pending, which designates the U.S. and which is hereby incorporated by reference in its entirety, and claims priority therefrom under 35 USC Section 120. This application also claims priority under 35 USC Section 119 from Korean Patent Application No. 10-2007-0035763, filed Apr. 11, 2007, the entire disclosure of which is also hereby incorporated by reference.

FIELD OF THE INVENTION

The present invention relates to a composition for the formation of a liquid crystal alignment layer.

BACKGROUND OF THE INVENTION

As the market for liquid crystal displays (LCDs) has expanded in recent years, there has been a continuing need for high-quality display devices. Further, as liquid crystal display devices have rapidly increased in size, there has been a growing need for high productivity manufacture of liquid crystal display devices for alignment layers. Under these circumstances, there is a continuously growing demand for high-performance materials sufficient to meet different requirements of various types of liquid crystal display devices that produce few defects in manufacturing processes and have excellent electro-optical properties and high reliability. Particularly, the alignment and electrical properties of liquid crystal molecules depending on the characteristics of liquid crystal alignment layers have a great influence on the image quality of LCDs using the liquid crystal alignment layers. In response to high display definition of LCDs, the requirements for the characteristics of alignment layers are becoming more stringent.

Active developments on all plastic displays (AODs) are being made nowadays. In a typical all plastic display, an aligning agent is coated on a low surface tension organic material. Thus, conventional LCD manufacturing processes require the use of aligning agents that exhibit better printability and faster curing at lower temperature as well as better electro-optical properties to improve the quality of LCDs. Since conventional polyimide-based aligning agents have low solubility, large amounts of low surface tension non-solvents cannot be introduced to improve the printability of the aligning agents.

It is known that the characteristics of alignment layers developed hitherto are greatly affected by the structures and characteristics of dianhydrides as monomers of materials for the alignment layers (Japanese Patent Nos. 2743460 and 3322089).

SUMMARY OF THE INVENTION

The present invention provides a composition for the formation of a liquid crystal alignment layer which comprises a polyimide synthesized using a dianhydride designed so as to exhibit excellent electro-optical properties and coating characteristics to impart excellent electro-optical properties in terms of voltage holding ratio and residual DC voltage and high solubility in solvents, thus achieving good printability on low surface tension substrates.

According to one aspect of the present invention, there is provided 3,4-dicarboxy-1,2,3,4-tetrahydro-6-t-butyl-1-naphthalenesuccinic dianhydride (hereinafter, referred to simply as 'tetracarboxylic dianhydride (TTDA)') represented by Formula 1:

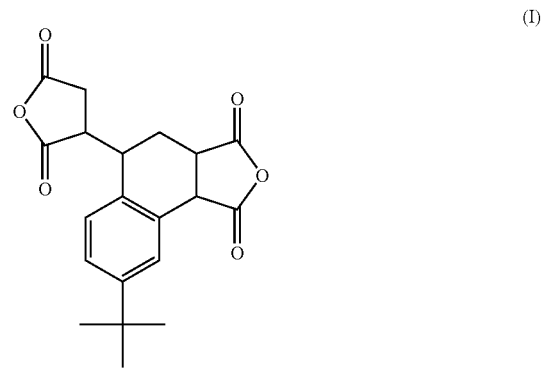

(I)

According to another aspect of the present invention, there is provided a liquid crystal aligning agent comprising a polyimide prepared from 3,4-dicarboxy-1,2,3,4-tetrahydro-6-t-butyl-1-naphthalenesuccinic dianhydride of Formula 1 and at least one diamine compound, and a solvent.

The polyimide includes a structural unit of Formula 2:

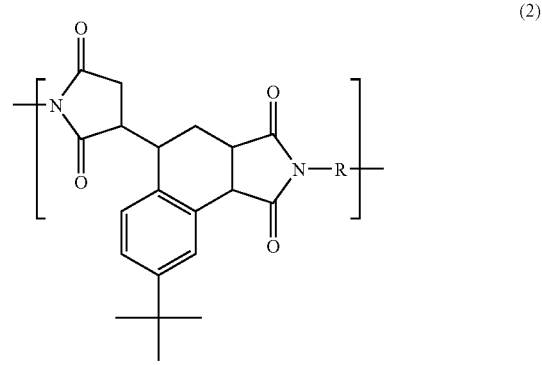

(2)

wherein R denotes a divalent organic group derived from a diamine compound, wherein about 1 to about 40 mol % of R is a divalent organic group derived from a diamine compound having $C_{10}$-$C_{30}$ linear, branched or alicyclic alkyl, $C_6$-$C_{30}$ aryl, $C_{10}$-$C_{30}$ arylalkyl or $C_6$-$C_{30}$ alkylaryl group, the alkyl being unsubstituted or substituted with one or more halogen atoms.

The polyimide can have a number average molecular weight of about 5,000 to about 500,000 g/mol.

The polyimide can be prepared by imidization of a polyamic acid.

According to yet another aspect of the present invention, there is provided a liquid crystal display device fabricated using the liquid crystal aligning agent. The liquid crystal aligning agent of the invention can provide a liquid crystal alignment layer for the liquid crystal display device that serves to control the alignment and movement of liquid crystal molecules on and under a liquid crystal layer of a liquid crystal display (LCD) device. The liquid crystal aligning agent of the present invention exhibits excellent electrical properties in terms of liquid crystal alignment properties, voltage holding ratio, pretilt angle and residual DC voltage, good printability, increased wash stability and improved resistance to defects. In addition, the liquid crystal aligning agent of the present invention can be used to form a liquid crystal alignment layer capable of being rapidly cured at low temperature.

BRIEF DESCRIPTION OF THE DRAWING

FIG. 1 is a $^1$H-NMR spectrum of 3,4-dicarboxy-1,2,3,4-tetrahydro-6-t-butyl-1-naphthalenesuccinic dianhydride prepared in Example 1.

DETAILED DESCRIPTION OF THE INVENTION

The present invention now will be described more fully hereinafter in the following detailed description of the invention, in which some, but not all embodiments of the invention are described. Indeed, this invention may be embodied in many different forms and should not be construed as limited to the embodiments set forth herein; rather, these embodiments are provided so that this disclosure will satisfy applicable legal requirements.

The present invention provides the tetracarboxylic dianhydride (TTDA) of Formula 1:

(1)

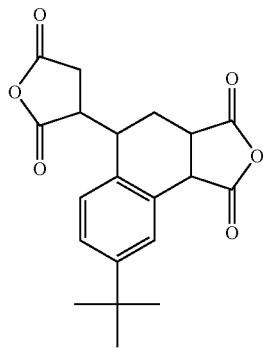

The tetracarboxylic dianhydride of the present invention can be synthesized via 2,4-cycloaddition and ene reaction of 4-tert-butylstyrene and maleic anhydride, as depicted by Reaction Scheme 1:

Scheme 1

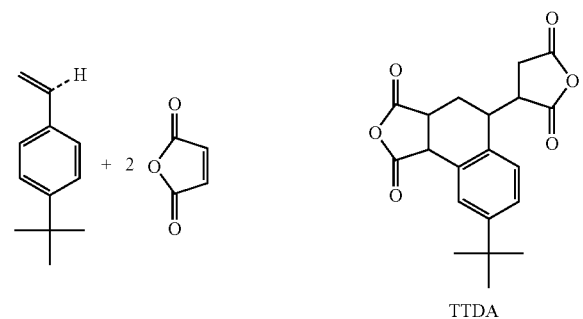

TTDA

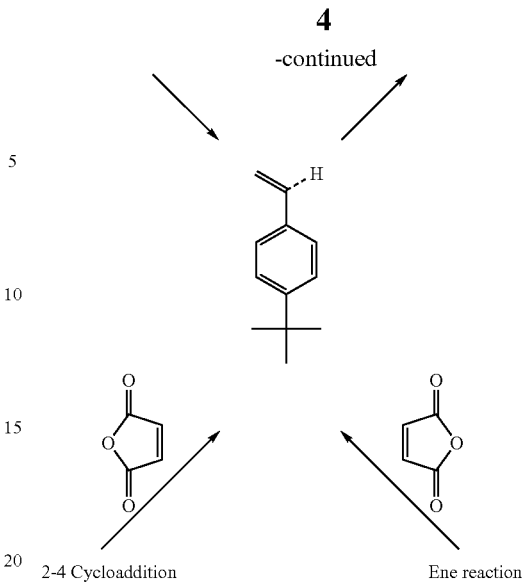

2-4 Cycloaddition          Ene reaction

The tetracarboxylic dianhydride of the present invention reacts with a diamine compound to prepare a polyimide. The polyimide can be used as an effective component of a liquid crystal aligning agent.

The present invention also provides a liquid crystal aligning agent comprising a polyimide prepared from 3,4-dicarboxy-1,2,3,4-tetrahydro-6-t-butyl-1-naphthalenesuccinic dianhydride of Formula 1 and at least one diamine compound, the polyimide having a structural unit of Formula 2:

(2)

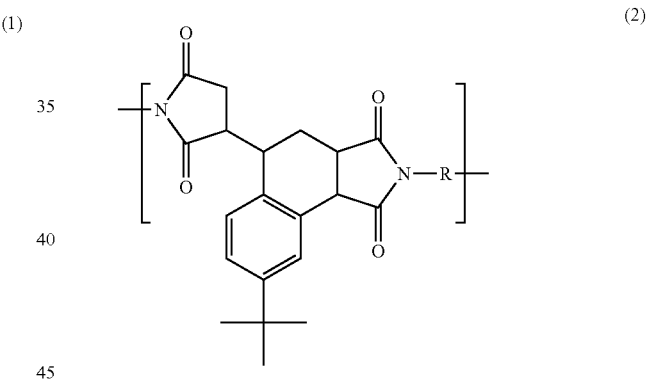

wherein R denotes a divalent organic group derived from a diamine compound, wherein about 1 to about 40 mol % of R is a divalent organic group derived from a diamine compound having $C_{10}$-$C_{30}$ linear, branched or alicyclic alkyl, $C_6$-$C_{30}$ aryl, $C_6$-$C_{30}$ arylalkyl or $C_6$-$C_{30}$ alkylaryl group in which the alkyl may be substituted with one or more halogen atoms, and a solvent.

The polyimide can have a number average molecular weight of about 5,000 to about 500,000 g/mol.

Any diamine compound may be used in the present invention so long as it is generally used for the polymerization of polyimides.

Examples of such diamine compounds include, but are not necessarily limited to, p-phenylenediamine (p-PDA), 4,4-methylenedianiline (MDA), 4,4-oxydianiline (ODA), m-bisaminophenoxydiphenylsulfone (m-BAPS), p-bisaminophenoxydiphenylsulfone (p-BAPS), 2,2-bisaminophenoxyphenylpropane (BAPP), 2,2-bisaminophenoxyphenylhexafluoropropane (HF-BAPP), 2,2'-dimethyl-4,4'-diaminobiphenyl, 3,3'-dimethyl-4,4'-diaminobiphenyl, and combinations thereof. The use of p-phenylenediamine (p-PDA) can improve the electrical properties and long-term stability of a liquid crystal alignment layer to be formed using the liquid crystal aligning agent.

In addition to the diamine compound, the polyimide can also include at least one functional diamine compound selected from compounds of Formulae 3, 4, 5 and 6:

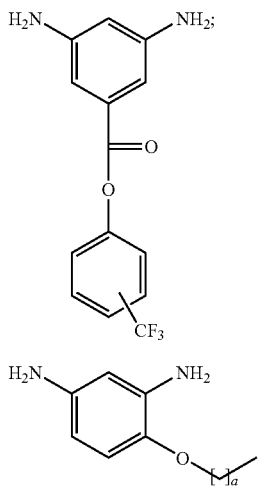
(3)

wherein a is an integer from 10 to 30;

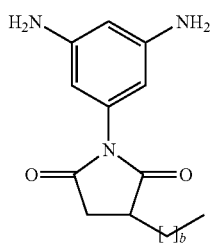
(5)

wherein b is an integer from 10 to 30; and

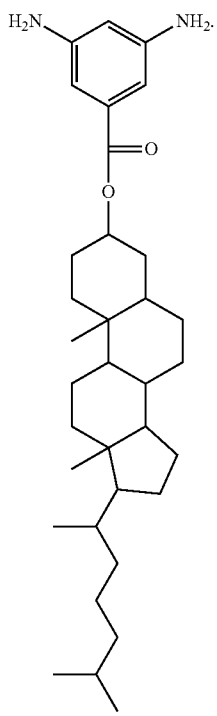
(6)

The content of the functional diamine compound may be from about 1 to about 40 mol %, for example about 3 to about 30 mol %, based on the total moles of the diamine compounds used for the preparation of the polyimide.

When the functional diamine compound is used in an amount of less than about 1 mol %, it may be difficult to achieve satisfactory pretilt of the aligning agent. Meanwhile, when the functional diamine compound is used in an amount greater than about 40 mol %, it may be difficult to synthesize a high molecular weight polymer for the formation of an alignment layer.

Examples of solvents suitable for use in the present invention include without limitation N-methyl-2-pyrrolidone (NMP), γ-butyrolactone, dimethylformamide (DMF), dimethylacetamide (DMAc), tetrahydrofuran (THF), ethyl cellosolve, butyl cellosolve, cyclopentanol, cyclohexanol, diethylene glycol diethyl ether, dipropylene glycol monoethyl ether, monoethylene glycol dimethyl ether, dipropylene glycol dimethyl ether, and the like, and combinations thereof.

The solids content of the liquid crystal aligning agent can range from about 1 to about 30%, for example about 3 to about 15%, and as another example about 5 to about 10%.

When the solids content is less than about 1%, the printing of the liquid crystal aligning agent may be affected by the surface of a substrate of an LCD device, causing deterioration in the uniformity of a film to be formed using the liquid crystal aligning agent. Meanwhile, when the solids content exceeds about 30% (i.e. the liquid crystal aligning agent is highly viscous), the uniformity of a film to be formed after printing of the liquid crystal aligning agent may be deteriorated and the transmittance of the film in an LCD device may be lowered.

In addition to the structural unit of Formula 2, the polyimide may further contain a structural unit prepared by the reaction of another tetracarboxylic dianhydride or at least one derivative thereof and a diamine compound to improve the electrical properties and mechanical properties of an alignment layer to be formed using the liquid crystal aligning agent.

Examples of suitable additional tetracarboxylic dianhydrides and derivatives thereof include, but are not limited to: aromatic cyclic dianhydrides, such as pyromellitic dianhydride (PMDA), biphthalic dianhydride (BPDA), oxydiphthalic dianhydride (ODPA), benzophenonetetracarboxylic dianhydride (BTDA) and hexafluoroisopropylidenediphthalic dianhydride (6-FDA); and alicyclic dianhydrides, such as 5-(2,5-dioxotetrahydrofuryl)-3-methylcyclohexene-1,2-dicarboxylic dianhydride (DOCDA), bicyclooctene-2,3,5,6-tetracarboxylic dianhydride (BODA), 1,2,3,4-cyclobutane-tetracarboxylic dianhydride (CBDA), 1,2,3,4-cyclopentanetetracarboxylic dianhydride (CPDA), 1,2,4,5-cyclohexanetetracarboxylic dianhydride (CHDA), 3,4-dicarboxy-1,2,3,4-tetrahydro-1-naphthalenesuccinic dianhydride (TDA) and 2,3,5-tricarboxycyclopentaneacetic dianhydride (TCA-AH); and the like, and combinations thereof.

The additional tetracarboxylic dianhydride or its derivative can be used in combination with TTDA so long as the characteristics of TTDA are not impaired. The content of the additional tetracarboxylic dianhydride or its derivative may be from about 1 to about 60 mol %, based on the total moles of the tetracarboxylic dianhydrides used for the preparation of the polyimide.

For the purpose of improving the alignment properties of the liquid crystal aligning agent according to the present invention, the polyimide may be terminated with aniline or maleic anhydride. A silane coupling agent or an epoxy compound may be additionally used to enhance the strength of a film to be formed using the liquid crystal aligning agent.

The polyimide can be prepared by thermal curing or chemical imidization of a polyamic acid precursor. The polyamic acid precursor is prepared by reacting the tetracarboxylic dianhydride with the diamine compound in an equivalent ratio of about 0.5:1 to about 1.5:1 in a solvent. The reaction conditions are controlled such that the polyamic acid precursor has a number average molecular weight of about 5,000 to about 500,000 g/mol. The solvent may be a general aprotic polar solvent, such as N-methyl-2-pyrrolidone (NMP), γ-butyrolactone (GBL), dimethylformamide (DMF), dimethylacetamide (DMAc) or tetrahydrofuran (THF). The reaction is carried out at a temperature of about −10° C. to about 100° C., for example about 0° C. to about 60° C.

Thereafter, the polyamic acid is heated to about 70 to about 200° C. at ambient pressure or about 200 to about 350° C. under pressure in a solvent, or is subjected to chemical imidization using pyridine and acetic anhydride in a solvent to prepare the final polyimide. The solvent can be without limitation N-methyl-2-pyrrolidone (NMP), γ-butyrolactone, dimethylformamide (DMF), dimethylacetamide (DMAc), or the like, or a combination thereof.

The present invention also provides a liquid crystal alignment layer formed by applying the liquid crystal aligning agent to a transparent electrode substrate, followed by heating. The present invention also provides a liquid crystal display device comprising the liquid crystal alignment layer.

Hereinafter, the present invention will be explained in more detail with reference to the following examples. However, these examples are given for the purpose of illustration and are not intended to limit the present invention.

EXAMPLES

Example 1

100 parts by weight of maleic anhydride, 12 parts by weight of benzene and 0.8 parts by weight of tolylhydroquinone are put into a reactor equipped with an agitator, a thermometer and a reflux condenser. The mixture is heated to about 120° C. and then 208 parts by weight of 4-tert-butylstyrene is slowly added thereto. After completion of the addition, the resulting mixture is refluxed at 120° C. for a total of 6 hours and 300 parts by weight of benzene is added thereto. The reaction mixture is cooled to room temperature and filtered, yielding TTDA in a yield of 60%. The product is found to have a melting point of 199-202° C. The structure of the product is identified by $^1$H-NMR spectroscopy (FIG. 1).

Example 2

0.95 moles of phenylenediamine and 0.05 moles of N-3,5-diaminophenyl-3-dodecylsuccinimide are put into a four-neck flask equipped with an agitator, a thermostat, a nitrogen injection system and a condenser under a stream of nitrogen gas. The mixture is dissolved using N-methyl-2-pyrrolidone (NMP). To the solution are added 0.6 moles of TTDA prepared in Example 1 and 0.4 moles of 1,2,3,4-cyclobutanetetracarboxylic dianhydride (CBDA), followed by vigorous stirring. The mixture is measured to have a solids content of 15 wt %. The mixture is allowed to react for 24 hours while maintaining the temperature at 30° C. to prepare a solution of polyamic acid (PA-1). 3.0 moles of acetic anhydride and 5.0 moles of pyridine are reacted with the polyamic acid at 80° C. for 6 hours. The reaction mixture is distilled ill vacuo to remove the catalyst and the solvents, yielding a soluble polyimide (PI-I). The polyimide is found to have a solids content of 30% and a number average molecular weight of 120,000 g/mol, as determined by gel-permeation chromatography (GPC).

The soluble polyimide is diluted with N-methyl-2-pyrrolidone (NMP) and butyl cellosolve (1:1) as solvents to prepare a solution (solids content: 5%) for the formation of an alignment layer.

Example 3

A soluble polyimide (PI-2) is prepared in the same manner as in Example 2 except that 0.85 moles of phenylenediamine and 0.15 moles of N-3,5-diaminophenyl-3-dodecylsuccinimide are used. The soluble polyimide is found to have a number average molecular weight of 120,000 g/mol, as determined by gel-permeation chromatography (GPC). A solution for the formation of an alignment layer is prepared using the soluble polyimide in accordance with the procedure described in Example 2.

Example 4

A soluble polyimide (PI-3) is prepared in the same manner as in Example 2 except that 0.85 moles of phenylenediamine, 0.15 moles of N-3,5-diaminophenyl-3-dodecylsuccinimide and 1.0 mole of TTDA are used. The soluble polyimide is found to have a number average molecular weight of 100,000 g/mol, as determined by gel-permeation chromatography (GPC). A solution for the formation of an alignment layer is prepared using the soluble polyimide in accordance with the procedure described in Example 2.

Comparative Example 1

A soluble polyimide (PI-4) is prepared in the same manner as in Example 2 except that 1.0 mole of 2,3,5-tricarboxycyclopentaneacetic dianhydride (TCA-AH) is used instead of TTDA to prepare a solution of polyamic acid. The soluble polyimide is found to have a number average molecular weight of 120,000 g/mol, as determined by gel-permeation chromatography (GPC). A solution for the formation of an alignment layer is prepared using the soluble polyimide in accordance with the procedure described in Example 2.

Comparative Example 2

A soluble polyimide (PI-5) is prepared in the same manner as in Example 4 except that 3,4-dicarboxy-1,2,3,4-tetrahydro-1-naphthalenesuccinic dianhydride (TDA) is used instead of TTDA. The soluble polyimide is found to have a number average molecular weight of 140,000 g/mol, as determined by gel-permeation chromatography (GPC). A solution for the formation of an alignment layer is prepared using the soluble polyimide in accordance with the procedure described in Example 2.

Comparative Example 3

A soluble polyimide (PI-6) is prepared in the same manner as in Example 2 except that 2,3,5-tricarboxycyclopentaneacetic dianhydride (TCA-AH) is used instead of TTDA. The soluble polyimide is found to have a number average molecular weight of 140,000 g/mol, as determined by gel-permeation chromatography (GPC). A solution for the formation of an alignment layer is prepared using the soluble polyimide in accordance with the procedure described in Example 2.

LCD cells are fabricated using the solutions prepared in Examples 2-4 and Comparative Examples 1-3 to evaluate the characteristics of the solutions. The results are shown in Table 1.

1) Fabrication of LCD Cells:

Each of the solutions is printed to a thickness of 0.1 μm on an ITO glass (10 cm×10 cm) and sequentially cured at 70° C. for one minute and at 220° C. for 10 minutes to form an alignment layer. The printed state of the solution is observed. The alignment layer is rubbed, sufficiently cleaned with isopropyl alcohol and purified water, and assembled to fabricate an LCD cell.

2) Evaluation of Printability:

Each of the solutions is applied to an ITO glass substrate to form an alignment layer. The spreadability of the solution is evaluated by visual observation and optical microscopy.

*Criteria for Evaluation of Spreadability:

0.001 ml of each of the solutions is dropped onto a clean ITO-coated glass substrate using a microsyringe and allowed to stand for 10-30 minutes. The spreadability of the liquid crystal aligning agent is evaluated by measuring the distance of the liquid crystal aligning agent spread from a position of the substrate where the liquid crystal aligning agent is dropped. Specifically, the spreadability of the liquid crystal aligning agent is judged to be 'good' when the distance is greater than 10 mm, 'fair' when the distance is between 5 and 10 mm, or 'poor' when the distance is shorter than 5 mm.

3) Measurement of Pretilt Angle:

The pretilt angle of the alignment layer of the LCD cell is measured by a crystal rotation method.

4) Measurement of Voltage Holding Ratio:

The voltage holding ratio of the LCD cell is measured at room temperature using VHRM105 (Atronics). Thereafter, the LCD cell is left standing in an oven at 60° C. for 100 hours and measured for voltage holding ratio. The reliability level of the LCD cell is determined by the following equation:

Reliability (%)=(Voltage holding ratio at room temperature/Voltage holding ratio after left standing in an oven at 60° C. for 100 hours)×100

5) Evaluation of Chemical Resistance:

A voltage of 2-4 V is applied to drive the LCD cell and observation is made as to whether defects and domains are formed by the cleaning solvents.

6) Evaluation of Curing Temperature*:

Each of the solutions is applied to an ITO glass substrate and cured for 10 minutes. The temperature at which 5% of the solvent is left during the curing is measured.

7) Measurement of Residual Amount of Solvent

Each of the solutions is printed to a thickness of 0.1 μm on an ITO glass substrate and sequentially cured at 70° C. for one minute and at 220° C. for 10 minutes. The amounts of the solvent remaining after the first and second curing steps are measured using a thermogravimetric analyzer (TGA), and its ratio is calculated.

TABLE 1

| Sample | Voltage holding ratio | | Reliability (%) | Pretilt angle (°) | Printability | Solvent residual amount (%) | Curing Temp. (° C.) | Chemical resistance (Defects) | Formation of domains |
|---|---|---|---|---|---|---|---|---|---|
| | Room temperature | 60° C. | | | | | | | |
| Example 2 | 99.5 | 99.0 | 99.5 | 8.1 | Good | 2.6 | 170 | Good | x |
| Example 3 | 99.6 | 99.1 | 99.5 | 89.4 | Good | 2.9 | 180 | Good | x |
| Example 4 | 99.5 | 98.6 | 99.1 | 89.3 | Good | 2.8 | 180 | Good | x |
| Comparative Example 1 | 99.4 | 95.4 | 99.0 | 6.6 | Fair | 5.1 | 220 | Poor | x |
| Comparative Example 2 | 99.3 | 97.7 | 98.3 | 89.0 | Fair | 6.7 | 230 | Poor | o |
| Comparative Example 3 | 99.3 | 96.6 | 97.3 | 7.4 | Fair | 4.3 | 210 | Poor | o |

The results in Table 1 show that the liquid crystal aligning agents prepared in Examples 2-4 and the liquid crystal alignment layers formed using the aligning agents have good printability, low curing temperatures and excellent characteristics in terms of chemical resistance and domain formation, as compared to the aligning agents prepared in Comparative Examples 1-3 and the liquid crystal alignment layers formed using the aligning agents. In addition, the aligning agents prepared in Examples 2-4 and the liquid crystal alignment layers formed using the aligning agents show higher voltage holding ratios at 60° C. and better reliability than the aligning agents prepared in Comparative Examples 1-3 and the liquid crystal alignment layers formed using the aligning agents. Furthermore, smaller amounts of the solvent are left on the alignment layers formed using the aligning agents prepared in Examples 2-4, indicating that the alignment layers have superior stability.

Many modifications and other embodiments of the invention will come to mind to one skilled in the art to which this invention pertains having the benefit of the teachings presented in the foregoing descriptions. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation, the scope of the invention being defined in the claims.

That which is claimed is:

1. A liquid crystal aligning agent comprising
a polyimide prepared by polymerization of an acid dianhydride of Formula 1:

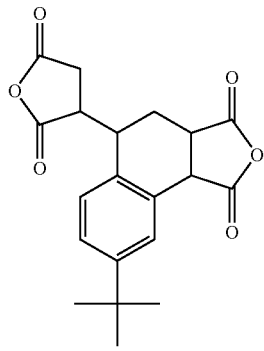
(1)

with at least one diamine compound, and
a solvent.

2. The liquid crystal aligning agent according to claim 1, wherein the polyimide comprises a structural unit of Formula 2:

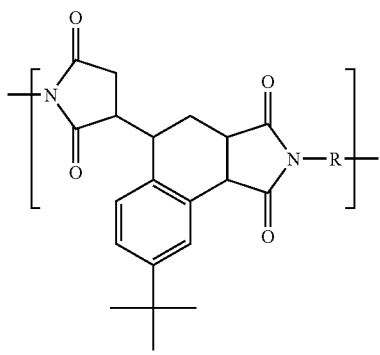
(2)

wherein R denotes a divalent organic group derived from a diamine compound, wherein about 1 to about 40 mol % of R is a divalent organic group derived from a diamine compound having $C_{10}$-$C_{30}$ linear, branched or alicyclic alkyl, $C_6$-$C_{30}$ aryl, $C_6$-$C_{30}$ arylalkyl or $C_6$-$C_{30}$ alkylaryl group, the alkyl being unsubstituted or substituted with one or more halogen atoms, and wherein the polyimide has a number average molecular weight of about 5,000 to about 500,000 g/mol.

3. The liquid crystal aligning agent according to claim 1, wherein the diamine compound comprises p-phenylenediamine (p-PDA), 4,4-methylenedianiline (MDA), 4,4-oxydianiline (ODA), m-bisaminophenoxydiphenylsulfone (m-BAPS), p-bisaminophenoxydiphenylsulfone (p-BAPS), 2,2-bisaminophenoxyphenylpropane (BAPP), 2,2-bisaminophenoxyphenylhexafluoropropane (HF-BAPP), 2,2'-dimethyl-4,4'-diaminobiphenyl, 3,3'-dimethyl-4,4'-diaminobiphenyl, or a combination thereof.

4. The liquid crystal aligning agent according to claim 1, wherein the diamine compound comprises at least one compound of Formulae 3, 4, 5 or 6, or a combination thereof.

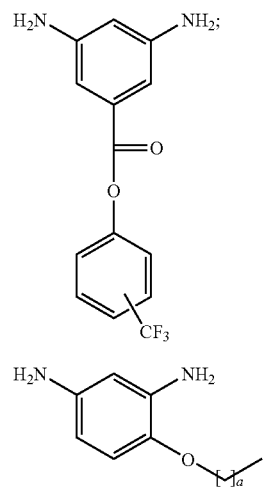
(3)

(4)

wherein a is an integer from 10 to 30;

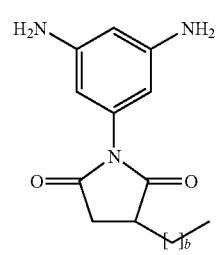
(5)

wherein b is an integer from 10 to 30; and

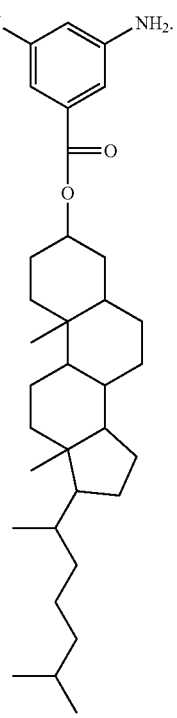
(6)

5. The liquid crystal aligning agent according to claim 1, wherein the polyimide is prepared by imidization of a polyamic acid.

6. The liquid crystal aligning agent according to claim 1, wherein the solvent comprises N-methyl-2-pyrrolidone (NMP), γ-butyrolactone, dimethylformamide (DMF), dimethylacetamide (DMAc), tetrahydrofuran (THF), ethyl cellosolve, butyl cellosolve, cyclopentanol, cyclohexanol, diethylene glycol diethyl ether, dipropylene glycol monoethyl ether, monoethylene glycol dimethyl ether, dipropylene glycol dimethyl ether, or a combination thereof.

7. The liquid crystal aligning agent according to claim 1, wherein the liquid crystal aligning agent has a solids content of about 1 to about 30%.

8. The liquid crystal aligning agent according to claim 1, wherein the polyimide further comprises a structural unit prepared by the reaction of a diamine compound with at least one tetracarboxylic dianhydride comprising pyromellitic dianhydride (PMDA), biphthalic dianhydride (BPDA), oxydiphthalic dianhydride (ODPA), benzophenonetetracarboxylic dianhydride (BTDA), hexafluoroisopropylidenediphthalic dianhydride (6-FDA), 5-(2,5-dioxotetrahydrofuryl)-3-methylcyclohexene-1,2-dicarboxylic dianhydride (DOCDA), bicyclooctene-2,3,5,6-tetracarboxylic dianhydride (BODA), 1,2,3,4-cyclobutanetetracarboxylic dianhydride (CBDA), 1,2,3,4-cyclopentanetetracarboxylic dianhydride (CPDA), 1,2,4,5-cyclohexanetetracarboxylic dianhydride (CHDA), 3,4-dicarboxy-1,2,3,4-tetrahydro-1-naphthalenesuccinic dianhydride (TDA), 2,3,5-tricarboxycyclopentaneacetic dianhydride (TCA-AH), or a combination thereof.

9. The liquid crystal aligning agent according to claim 8, wherein the content of the structural unit is from about 1 to about 60 mol %, based on the total structural units of the polyimide.

10. A liquid crystal alignment layer formed using the liquid crystal aligning agent according to claim 1.

11. A liquid crystal display device comprising the liquid crystal alignment layer according to claim 10.

12. A polyimide prepared by polymerization of an acid dianhydride of Formula 1:

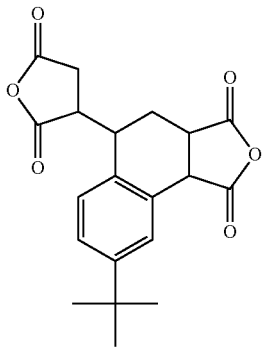

with at least one diamine compound, wherein said polyimide has a number average molecular weight of about 5,000 to about 500,000 g/mol.

13. The polyimide according to claim 12, wherein the polyimide comprises a structural unit of Formula 2:

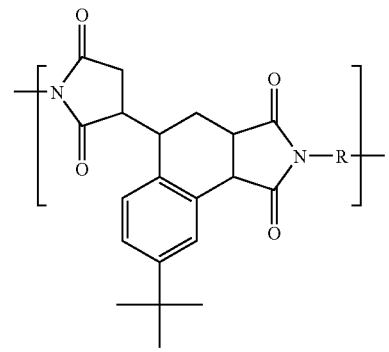

wherein R denotes a divalent organic group derived from a diamine compound, wherein about 1 to about 40 mol % of R is a divalent organic group derived from a diamine compound having $C_{10}$-$C_{30}$ linear, branched or alicyclic alkyl, $C_6$-$C_{30}$ aryl, $C_6$-$C_{30}$ arylalkyl or $C_6$-$C_{30}$ alkylaryl group, the alkyl being unsubstituted or substituted with one or more halogen atoms, and wherein the polyimide has a number average molecular weight of about 5,000 to about 500,000 g/mol.

14. The polyimide according to claim 13, wherein the diamine compound comprises p-phenylenediamine (p-PDA), 4,4-methylenedianiline (MDA), 4,4-oxydianiline (ODA), m-bisaminophenoxydiphenylsulfone (m-BAPS), p-bisaminophenoxydiphenylsulfone (p-BAPS), 2,2-bisaminophenoxyphenylpropane (BAPP), 2,2-bisaminophenoxyphenylhexafluoropropane (HF-BAPP), 2,2'-dimethyl-4,4'-diaminobiphenyl, 3,3'-dimethyl-4,4'-diaminobiphenyl, or a combination thereof.

15. The polyimide according to claim 13, further comprising at least one functional diamine compound of Formulae 3, 4, 5 or 6, or a combination thereof:

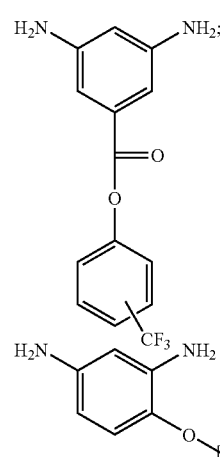

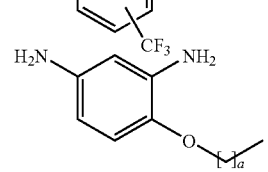

wherein a is an integer from 10 to 30;

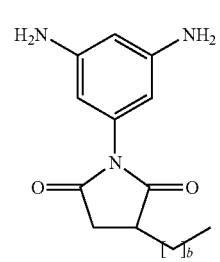

-continued

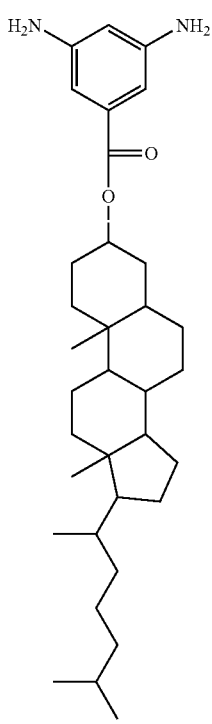

(6)

wherein b is an integer from 10 to 30.

16. The polyimide according to claim 15, wherein said polyimide comprises said functional diamine compound in an amount of about 1 to about 40 mol %, based on the total moles of diamine compounds.

17. The polyimide according to claim 12, wherein the polyimide further comprises a structural unit prepared by the reaction of a diamine compound with at least one tetracarboxylic dianhydride comprising pyromellitic dianhydride (PMDA), biphthalic dianhydride (BPDA), oxydiphthalic dianhydride (ODPA), benzophenonetetracarboxylic dianhydride (BTDA), hexafluoroisopropylidenediphthalic dianhydride (6-FDA), 5-(2,5-dioxotetrahydrofuryl)-3-methylcyclohexene-1,2-dicarboxylic dianhydride (DOCDA), bicyclooctene-2,3,5,6-tetracarboxylic dianhydride (BODA), 1,2,3,4-cyclobutanetetracarboxylic dianhydride (CBDA), 1,2,3,4-cyclopentanetetracarboxylic dianhydride (CPDA), 1,2,4,5-cyclohexanetetracarboxylic dianhydride (CHDA), 3,4-dicarboxy-1,2,3,4-tetrahydro-1-naphthalenesuccinic dianhydride (TDA), 2,3,5-tricarboxycyclopentaneacetic dianhydride (TCA-AH), or a combination thereof.

18. The polyimide according to claim 17, wherein the content of the structural unit is from about 1 to about 60 mol %, based on the total structural units of the polyimide.

* * * * *

UNITED STATES PATENT AND TRADEMARK OFFICE
CERTIFICATE OF CORRECTION

PATENT NO.        : 7,901,745 B2
APPLICATION NO.   : 12/476465
DATED             : March 8, 2011
INVENTOR(S)       : Jae Min Oh, Tae Hyoung Kwak and Ji Young Jeong It is certified that error appears in the above-identified patent and that said Letters Patent is hereby corrected as shown below:

In the Specification:

Column 2, Line 53 reads: "aryl, ~~$C_{10}$-$C_{30}$~~ arylalkyl or $C_6$-$C_{30}$ alkylaryl group, the alkyl" and should read: "aryl, $\underline{C_6\text{-}C_{30}}$ arylalkyl or $C_6$-$C_{30}$ alkylaryl group, the alkyl"

Column 8, Line 2 reads: "for 6 hours. The reaction mixture is distilled ~~ill~~ vacuo to" and should read: "for 6 hours. The reaction mixture is distilled $\underline{in}$ vacuo to"

In the Claims:

Column 15, Claim 15, Compound 6 is incorrectly depicted as:

Signed and Sealed this
Seventeenth Day of May, 2011

David J. Kappos
*Director of the United States Patent and Trademark Office*

CERTIFICATE OF CORRECTION (continued)
U.S. Pat. No. 7,901,745 B2

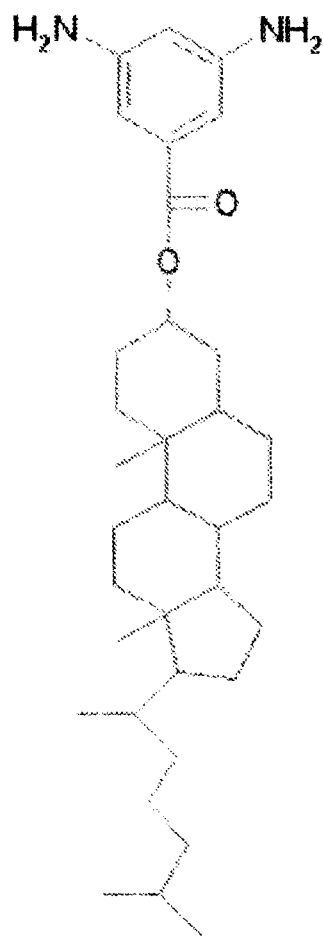

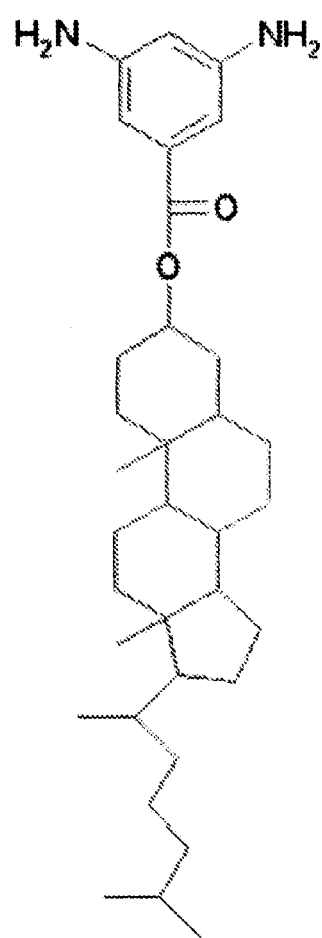

and should be depicted as: